United States Patent
Bolton et al.

(10) Patent No.: US 7,591,861 B2
(45) Date of Patent: Sep. 22, 2009

(54) PROCESSES TO PRE-TREAT HAIR WITH ORGANIC SOLVENTS

(75) Inventors: Philip David Bolton, Beverly (GB); Jennifer Mary Marsh, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 44 days.

(21) Appl. No.: 11/900,559

(22) Filed: Sep. 12, 2007

(65) Prior Publication Data
US 2008/0256724 A1 Oct. 23, 2008

(51) Int. Cl.
*A61Q 5/10* (2006.01)
(52) U.S. Cl. .................. 8/405; 8/406; 8/428; 8/435; 8/492; 8/542; 132/202; 132/208
(58) Field of Classification Search .......... 8/405, 8/406, 428, 435, 492, 542; 132/202, 208
See application file for complete search history.

(56) References Cited

U.S. PATENT DOCUMENTS

| | | | |
|---|---|---|---|
| 4,801,302 A * | 1/1989 | Grollier | 8/429 |
| 5,609,860 A | 3/1997 | Tabata et al. | |
| 6,274,150 B1 * | 8/2001 | Simonnet et al. | 424/401 |
| 2004/0216248 A1 * | 11/2004 | Nocker et al. | 8/406 |

FOREIGN PATENT DOCUMENTS

| EP | 1291006 A | 3/2003 |
|---|---|---|
| EP | 1302195 A | 4/2003 |
| EP | 1428497 A | 6/2004 |
| JP | 54140739 A * | 11/1979 |
| JP | 08359737 | * 12/1996 |
| JP | 10182373 A | 7/1998 |
| JP | 2000169344 A | 6/2000 |
| WO | WO0197756 A | 12/2001 |

OTHER PUBLICATIONS

English Abstract of the Patent No. JP 08359737 (Dec. 1996).*
English Abstract of the Patent No. JP54140739 A (Nov. 1979).*
Global New Products Database, ID 990455 (Dec. 2006).
Global New Products Database, ID 635252 (Oct. 2008).

* cited by examiner

*Primary Examiner*—Eisa B Elhilo
(74) *Attorney, Agent, or Firm*—Melissa Krasovec; Marianne Dressman; Tara Rosnell

(57) ABSTRACT

The present invention discloses methods and kit-of-parts for treating keratinous fibres prior to dyeing to control and modulate dye uptake into the fibre. Organic solvents having log P of from −4.0 to −0.5 or from 0.5 to 4.0 are used to manufacture pre-treatment composition to be applied to the hair. When the hair is pre-treated with at least one organic solvent having a log P of from 0.5 to 4.0 the dye penetration into the keratinous fibres is enhanced, while pre-treating the hair with at least one organic solvent having a log P of from −4.0 to −0.5 reduces the dye uptake. One or more compositions to pre-treat the keratinous fibres can be effortlessly applied on different zones of the hair and can be left in place or removed prior the application of the dyeing composition.

3 Claims, No Drawings

PROCESSES TO PRE-TREAT HAIR WITH ORGANIC SOLVENTS

FIELD OF THE INVENTION

The present invention relates to methods to treat keratinous fibres with organic solvents prior to dyeing to enhance or reduce the dye penetration into the fibre. Furthermore, the present invention relates to the use of organic solvents to manufacture cosmetic compositions to be used in said methods and kits comprising said cosmetic compositions.

BACKGROUND OF THE INVENTION

Dyeing keratinous fibres, especially human hair, has become a routine method to accommodate the changes in fashion and style and to provide coverage of grey hair.

Numerous products are available to perform dyeing and a great variety of shades and tones can be achieved for almost any colour and type of hair.

Nevertheless, once virgin hair has been coloured, subsequent colouring events are found to be difficult in providing either the same overall colour appearance or natural colour variations.

Particularly, the tips of coloured keratinous fibres exhibit more damage than the root portion. This is not only due to the high number of dyeing events that the tip portions have undergone. The combination of reduced delivery to the tips of moisturizing and emollient substances naturally secreted by sebaceous glands of the scalp, the increased exposure to the aggressive environmental conditions and the rubbing against clothes, especially in long hair, are additional circumstances which are also known to cause further hair tip damage.

Damaged keratinous fibres present a heterogeneously altered structure of the outer hydrophobic layer, creating variable substrates for the next colouring event. This variety of substrates results in altered uptake of dye into the fibres during dyeing. Virgin or less coloured keratinous fibres, as those found in the roots, uptake dyes differently from those in the porous tips that have been undergoing several dyeing events. The outcome is the formation of very different and unexpected colours, resulting in an overall effect which is unlikely to be desirable.

Efforts in applying the dyeing compositions for a longer time period onto the root than onto the tips have been confirmed to be inefficient to provide a homogenous root-to-tip evenness and do not particularly improve targeted grey coverage.

Attempts to reformulate the conventional oxidative dye compositions already available with ingredients capable of providing homogenous root-to-tip evenness, targeted grey coverage or natural colour variation are difficult and expensive.

Often reformulations of the conventional chassis lead to dye/medium phase separation, pH variation, by-products and heat formation, high degradation of dyes and formation of highly irritant intermediates. Besides, reformulations of the conventional chassis are unlikely to deliver the traditional colours and tone shades, which are appreciated and expected by habitual users.

Finally, cosmetic compositions that are used on human hair, besides providing the aesthetic expected results must be unobjectionable in regard to toxicological and dermatological properties and must provide fastness to a permanent wave treatment, acid fastness and fastness to rubbing.

To overcome the above mentioned problems, different approaches have already been proposed in the art. WO 99/55295 discloses a method to treat mammalian wet or dry hair with a composition comprising a hydrophobic and/or cationic conditioning agent. U.S. Pat. No. 6,497,888 discloses a process to limit the penetration into skin and/or keratinous fibres of active agents by applying to the skin and/or to keratinous fibres a composition comprising a dispersion of vesicles enclosing a ceramide. U.S. Pat. No. 5,500,218 discloses a preparation for preventing the colouring of skin adjoining the hair line when dyeing the hair. Said preparation is hydrophobic, viscous and has glue-like consistency as it comprises polyethylene glycols, alkoxylated fatty acids and polyols, which makes it a waxy barrier to the dye. EP 1238649 discloses a hair dye composition to be used at a pH of from 2 to 6 comprising a compound having a 5 to 6 membered lactone skeleton and an acid dye.

However, there still remains a desire to provide methods to pre-treat the hair prior to a dyeing event to obtain root-to-tip evenness, targeted grey coverage and/or natural colour variation. The methods should be flexible enough to control and modulate dye uptake and to be used with the conventional oxidative dye chassis, which work at basic pH without having to reformulate the already commercially available dyeing compositions.

SUMMARY OF THE INVENTION

Accordingly, it is an object of the present invention to provide a method for treating hair comprising the steps of contacting the hair with a pre-treatment composition comprising at least one organic solvent having a log P of from −4.0 to −0.5 or from 0.5 to 4.0, wherein said organic solvent is present in said pre-treatment composition at a level of from 10% to 100% and by applying a hair dyeing composition to the hair.

The present invention is also directed to kits comprising pre-treatment compositions for treating the hair according to this method.

The present invention is further directed to the use of at least one solvent having log P ranges as described above to manufacture pre-treatment compositions to treat keratinous fibre prior dyeing.

These and other features, aspects and advantages of the present invention will become evident to those skilled in the art from a reading of the present disclosure.

DETAILED DESCRIPTION OF THE INVENTION

While the specification concludes with claims, which particularly point out and distinctly claim the invention, it is believed the present invention will be better understood from the following description.

As used herein the term 'hair' to be treated may be 'living' i.e. on a living body or may be 'non-living' i.e. in a wig, hairpiece or other aggregation of non-living keratinous fibers. Mammalian, preferably human hair is preferred. However, wool, fur and other keratin containing fibers are suitable substrates for the compositions according to the present invention.

As used herein, the term 'organic solvent' refers to "a component of a solution which is present in excess, or whose physical state is in the same as that of the solution". As water falls within this definition (from Chambers Science and Technology Dictionary published jointly by W&R Chambers and Cambridge University Press 1988), the term "organic solvent" as used herein expressly excludes water.

As used herein the term 'dyeing composition' is used in the broad sense and it is intended to encompass all the treatments of hair comprising at least one step of contacting the hair with at least one dyeing component. Correspondingly, the term 'dyeing event' is used broadly to encompass any treatment of contacting the hair with a dyeing component.

As used herein, the term 'oxidising composition' means a composition comprising at least one oxidising agent suitable for use on hair, such as hydrogen peroxide, sodium, potassium, ammonium or other salts of perborate, percarbonate, persulfate or percarbamide. Non-limiting examples of such compositions are oxidative dye compositions and bleaching compositions.

As used herein the term 'oxidative treatment of hair' or a 'hair treatment comprising at least one oxidative step' is used in the broad sense that it is intended to encompass all treatments of hair comprising at least one step of contacting hair with at least one oxidising composition. Preferred examples of such of oxidative treatment for human hair are bleaching, oxidative dyeing or perming.

As used herein, the term 'immediately' means within about 60 minutes, preferably within about 30 minutes, even more preferably within about 5 minutes and even more preferably within about 1 minute.

All percentages are by weight of the weight of the total composition unless specifically stated otherwise. When more than one organic solvent is used during a pre-treatment, the total weight to be considered is the total weight of all the organic solvents applied on hair simultaneously (i.e. the weight found 'on-head') unless otherwise specified. All ratios are weight ratios unless specifically stated otherwise.

All cited references are incorporated herein by reference in their entireties. Citation of any reference is not an admission regarding any determination as to the availability as prior art to the claimed invention.

In examining how to solve the above technical problem, the present inventor moved away from the delivery of a pre-treatment composition comprising conditioning agents. These methods of pre-treatment deliver cosmetic properties to the hair such as softness, smoothness and disentangling, but fail to provide appreciable natural colour variation, efficient grey coverage and root-to-tip evenness. It has now been discovered that organic solvents, having log P of from about −4.0 to about −0.5 or from about 0.5 to about 4.0, when applied onto the hair prior to a dyeing composition, are capable of modulating and effectively controlling the dye penetration into the hair, thus, enabling intense or subtle colouration to be obtained where it is specifically required.

According to the present invention organic solvents are used to manufacture pre-treatment compositions to treat the hair prior to dyeing. It has been surprisingly found that when the hair is treated with such pre-treatment compositions comprising at least one organic solvent having Log P of from −4.0 to −0.5 or from 0.5 to 4.0 to manufacture a pre-treatment composition to treat hair prior to dyeing, wherein the organic solvent is present in said pre-treatment composition at a level of from about 10% to about 100%, preferably from about 15% to about 100%, more preferably from about 25% to about 100%, even more preferably from about 50% to about 98.99% by weight of the total composition the dye intake can be controlled. In particular, when the organic solvents used to manufacture the pre-treatment composition have a log P of from −4.0 to −0.5 then the dye intake can be reduced during the subsequent hair dyeing. On the contrary, when the organic solvent used has a log P of from about 4.0 to about 0.5 then the dye intake can be increased.

Thereby, the dye intake may be regulated according to the hair colour present and/or to the result that is to be achieved.

Without being bound by theory, it is believed that when applying to the hair an organic solvent with negative log P before applying a dyeing composition, the amount of dye material that it is delivered into the keratinous fibres can be reduced, compared to the amount of dye, which would normally penetrate the fibres without the application of the pre-treatment composition. Correspondingly, when an organic solvent with positive log P is applied, the dye uptake into the fibres can be increased.

The technical rational behind these effects are that the hydrophobic dye precursors are less likely to transit the hydrophilic region created over the hair when the hair are pre-treated with hydrophilic solvents, which have negative log P. In the converse situation, when a more hydrophobic solvent having positive log P is applied to the hair, a more favourable environment is created for the hydrophobic dye precursors to penetrate into the fibres.

The organic solvents suitable for use herein must have a partition coefficient (octanol-water) (log P) at 25° C. of from about −4.0 to about −0.5 or from about 0.5 to about 4.0.

The definition of log P as used herein serves as an index of partition of a substance between an octanol phase and a water phase and is defined by the following formula:

$$\text{Log } P = \log([\text{substance}]_{octanol}/[\text{substance}]^{water})$$

wherein $[\text{substance}]_{octanol}$ and $[\text{substance}]_{water}$ represent the concentration expressed in mol of the substance in the octanol phase and that in the water phase, respectively.

In the present invention the log P calculations were carried out using commercially available software called ACD Labs Log P from Advanced Chemistry Development Labs (Head Office—Advanced Chemistry Development, Inc. 110 Yonge Street, 14th floor, Toronto, Ontario, Canada M5C 1T4).

This software has the unique additive-constitutive ACD/log P algorithm in common. The ACD/log P algorithm is based on well-characterised log P contributions of separate atoms, structural fragments, and intermolecular interactions between different fragments. These contributions have been derived from ACD/Labs internal database of over 18,400 structures for which one or more experimental log P values have been reported in the literature. This database can be directly viewed as part of the program Solvents Any solvent having the above described properties can be employed in the present invention. Examples of solvent classes useful herein are, but are not limited to, alcohols, alkoxylated alcohols, aryloxylated alcohols, polyols, glyceryl esters, polymeric ethers, ketones, hydrocarbons and mixtures thereof.

Suitable solvents are benzyl alcohol, benzyl benzoate, 2-benzyloxyethanol, benzyl glycol, 1,2-butanediol, 1,3-butanediol, 1,4-butanediol, 2,3-butanediol, butoxydiglycol, butoxyethanol, butoxyethyl acetate, butyl acetate, t-butyl acetate, n-butanol, t-butanol, butylene glycol, butylene glycol proprionate, butyloctanol, butyloctyl benzoate, C7-8 Isoparaffin, C8-9 Isoparaffin, C9-11 Isoparaffin, C9-13 isoparaffin, cyclohexane, cyclohexanedimethanol, cyclohexanone, decane, 1,10-decanediol, dodecene, diethoxydiglycol, diethylene glycol, diethylene glycol mono-n-butyl ether, dimethoxydiglycol, dimethyl ether, dimethyl glutarate, dimethyl maleate, dimethyl oxalate, dimethyl sulfone, dioxolane, dipropylene glycol, dipropylene glycol dimethyl ether, dipropyl oxalate, docenene, ethoxydiglycol, ethoxydiglycol acetate, ethoxyethanol, ethoxyethanol acetate, ethyl acetate, ethyl ether, ethylene glycol, ethylene glycol mono-n-butyl ether, ether hexanediol, ethylhexyl acetate, ethylhexyl benzoate, ethyl lactate, glycerine, glycol, heptane, hexadecane, hexane, hexanediol, 1,2-hexanediol, 1,2,6-hexanetriol, hexane, hexyl alcohol, hexylene glycol, isobutoxypropanol, isododecane, isooctane, isopentane, isopentyldiol, isopropyl acetate, isopropyl alcohol, 3-methoxybutanol, methoxybutanol, methoxyethanol, methoxyisopropanol, methoxymethylbutanol, methyl acetate, methyl hexyl ether, 4-methyl-2-pentanone, octane, pentane, 1,5-pentanediol, pentylene glycol, 2-phenoxyethanol, 1-phenoxy-2-propanol, phenoxypropanediol, 2-phenyethanol, phenylpropanol, propanediol, propyl acetate, propyl alcohol, propylene glycol, trimethyl-1,3-pentanediol.

The organic solvents useful herein have preferably a molecular weight of about 200 or less, more preferably about 185 or less, even more preferably about 160 or less.

The total amount of the solvent used is from about 10% to about 100% by weight of the total pre-treatment composition, preferably from about 15% to about 100%, more preferably from about 25% to about 100% and particularly preferably from about 50% to about 98.99% by weight of the total pre-treatment composition.

An organic solvent having a partition co-efficient (octanol-water) (log P) of between about 0.5 and about 4.0 is expected to deliver improved dye performance versus no pre-treatment and will herein be referred to as 'dye up'.

Specific solvent examples that deliver the above benefit include ethylene glycol mono-n-butyl ether (log P=0.8), cyclohexanone (0.76), n-butanol (0.88), diethylene glycol mono-n-butyl ether (0.9), benzyl alcohol (1.1), 1-phenoxy-2-propanol (1.1), 2-benzyloxyethanol (1.2), 2-phenoxyethanol (1.2), 2-phenylethanol (1.2) and 4-methyl-2-pentanone (1.25) and mixtures thereof. Of these, n-butanol (0.8), cyclohexanone (1.2) and 4-methyl-2-pentanone (1.2) and mixtures thereof are preferred.

An organic solvent having a partition co-efficient (octanol-water) (log P) of between −0.5 and −4.0 is expected to deliver decreased dye performance versus no pre-treatment and will herein be referred to as 'dye down'.

Specific examples include lower polyols such as ethylene glycol (log P=−1.4), propylene glycol (−1.1), 1,3 butanediol (−1.4), diethylene glycol (−1.3), dipropylene glycol (−0.66) and glycerine (−2.32) or mixtures thereof. Of these, diethylene glycol (−1.51) and glycerine (−2.2) or mixture thereof are preferred. Glycerine is the most preferred solvent.

Additional Components

The pre-treatment composition may further comprise additional adjuncts, which are selected so as not to eliminate or substantially reduce the performance or shelf stability of the composition. The additional ingredients, comprised in the pre-treatment composition or used in combination therewith are discussed in detail later herein and may include, but are not limited to, buffering agents, hair dyeing agents such as oxidative dye precursors, non-oxidative dyes, alkalizing agents, thickeners, solvents, enzymes, anionic, non ionic, amphoteric and cationic surfactants, carriers, antioxidants, stabilizers, perming actives, perfumes, masking fragrances, herb and plant extracts, pearlescent, opacifiers, hair swelling agents and/or polymers, humectants, moisturizers, viscosity enhancers, gelling agents, chelators, UV filters, antimicrobials, preservatives, proteins and/or mixtures thereof.

Method of Use

According to the present invention the method of treating performed herein is particularly versatile and can be potentially used with any type of dyeing composition.

One or more pre-treatment compositions are applied onto dry or wet hair and then they are worked thoroughly or just on a defined section of the hair, such as on selected strands, on the roots or on the tips. The application of the pre-treatment composition can be accomplished by the user with the hands or employing tools, such gloves, combs and brushes. The pre-treatment composition is left in place enough long to ensure uniform and complete application. Typically the pre-treatment composition is left on the hair for about 60 minutes, preferably about 30 minutes, more preferably about 5 minutes and even more preferably about 1 minute before to apply the dyeing composition. The pre-treatment composition may be left on place on the hair before applying a hair dyeing composition or may be rinsed off the hair.

One or more pre-treatment compositions can be applied within the same dyeing event. For example, when more than one pre-treatment composition is applied, compositions comprising organic solvents having positive log P may be applied onto portions of hair, which are separated from those areas where pre-treatment compositions comprising organic solvents having negative log P are applied.

The use of organic solvents with either positive or negative log P to pre-treat the hair allows the user to obtain diverse final results.

The application of organic solvents onto only selected strand of hair allows the user to obtain a controlled dye up or dye down depending whether the organic solvents used have a positive or negative log P. The application of organic solvents only onto selected strands may be performed by pinching the hair with the user's fingers or by employing tools and devices such combs, brushes, bristles, etc. As the organic solvents are applied only and specifically onto certain strands of hair, the subsequent dyeing event will provide more dye or less dye only onto the strands which have been pre-treated with the organic solvents. The final result achieved by this method is a multi-tonal colour. The choice of the organic solvent will allow the user to select the intensity of the tone, from a more subtle and natural multi tone using organic solvents with low log Ps to more bold and pronounced tones using organic solvents with higher log P.

An efficient grey coverage can be performed by employing hydrophobic organic solvents having a positive log P and thus, providing dye up.

The user applies the pre-treatment composition in the area where the newly grown hair presents more occurrence of de-pigmentation. As the hydrophobic organic solvents are applied specifically onto the grey or white hair, this hair will receive more dye than without pre-treatment, thus, the final effect obtained is a more homogenous colouration of the root hair with the rest of the hair.

The method of the present invention is of a considerable benefit to avoid the pronounced penetration of dyes in porous damaged tips, hence, allowing an improved root-to-tips evenness. By applying hydrophilic organic solvents only on the tips, it is possible to reduce the amount of dye penetration during the following dying event. The final result is a more homogenous coloration without having tips with a striking temporary colouration, which easily fade after shampoos leaving the tips colour as "washed-out".

One or more pre-treatment compositions can be applied immediately before the dyeing composition. The pre-treatment compositions can be rinsed off hair before the application of the dyeing compositions, but will be preferably kept on the hair during the application of the dyeing compositions, the resulting mixture being rinsed off following the dyeing event.

Kit

The pre-treatment compositions of the present invention may be sold separately or preferably as part of a bleaching or colouring kit comprising single packaged containers as described herein below. The kit may further comprise a tool to apply the pre-treatment composition onto the hair.

Oxidising compositions to perform a dyeing event are usually sold in kits comprising, in individually packaged components such as separate containers, a first container comprising a dye component (also called "dye cream" for emulsions or "dye liquid" for solutions) comprising the oxidative dye, precursors and an alkalizing agent which is typically ammonia in a suitable carrier and a second container comprising a hydrogen peroxide component (also called "hydrogen peroxide cream" for emulsions or "hydrogen peroxide liquid" for solutions) comprising the oxidizing agent (usually hydrogen peroxide). The consumer mixes the dye component and oxidising agent together immediately before use and applies it onto the hair.

Similarly, bleaching compositions are also usually sold as a kit comprising two or three individually packaged components typically in two or three separate containers. A first component comprises the ammonium ion source (e.g. ammonia), a second component comprises the oxidizing agent and a third (optional) component comprises a second oxidizing agent. The bleaching compositions are obtained by mixing the above-mentioned components immediately before use.

Non oxidative colouring compositions typically are also sold as a kit and contain one or two individually packaged components, the first containing the dyeing composition and optionally the second containing a post dyeing treatment conditioner.

The hair colouring or bleaching compositions of such kits may comprise at least one source of an oxidizing agent.

Preferred oxidizing agents for use herein are water-soluble peroxygen oxidizing agents. "Water-soluble" as defined herein means that in standard condition at least about 0.1 g, preferably about 1 g, more preferably about 10 g of said oxidizing agent can be dissolved in 1 liter of deionized water. The oxidizing agents are valuable for the initial solubilisation and decolorisation of the melanin (bleaching) and accelerate the polymerization of the oxidative dye precursors (oxidative dyeing) in the hair shaft.

Preferred water-soluble oxidizing agents are inorganic peroxygen materials capable of yielding hydrogen peroxide in an aqueous solution. Water soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Mixtures of two or more such oxidizing agents can be used if desired. Preferred for use in the compositions according to the present invention is hydrogen peroxide.

The level of the oxidizing agent in the oxidizing composition is of from about 0.5% to about 20% by weight, more preferably of from about 1% to about 15, even more preferably from about 0.1% to about 7% by weight.

Hair colouring compositions comprise but are not limited to oxidative dyeing compositions. Such compositions comprise oxidative hair dye precursors also known as primary intermediates and couplers that will deliver a variety of hair colours to the hair.

These compounds are well known in the art, and include aromatic diamines, aminophenols and their derivatives (a representative but not exhaustive list of oxidation dye precursor can be found in Sagarin, "Cosmetic Science and Technology", "Interscience, Special Edn. Vol. 2 pages 308 to 310).

Precursors can be used with couplers. Couplers are generally colourless molecules that can form colours in the presence of activated precursors.

The choice of precursors and couplers will be determined by the colour, shade and intensity of coloration that is desired. The precursors and couplers can be used herein, singly or in combination, to provide dyes having a variety of shades ranging from ash blonde to black. Hair dye compositions will generally comprise from about 0.001% to about 10%, preferably from about 0.1% to about 2%, of oxidative dye precursors and couplers.

In one embodiment of the present invention a kit may comprise at least one individually packaged pre-treatment composition comprising at least one organic solvent having Log P from about −0.4 to about −0.5 and/or from about 0.5 to about 4.0, wherein the organic solvent is present in said pre-treatment composition at a level of from about 10% to about 100%, preferably from about 15% to about 100%, more preferably from about 25% to about 100%, even more preferably from about 50% to about 98.99% by weight of the total composition, and an individually packaged composition comprising at least one oxidative dye precursor, and an individually packaged composition comprising at least one oxidizing agent.

The hair colouring or bleaching compositions of such kits may comprise at least one conditioning agent. The conditioning agent will generally be used at levels from about 0.05% to about 20% by weight of the composition, preferably of from about 0.1% to about 15%, more preferably of from about 0.1% to about 15%, more preferably of from about 0.2% to about 2%. The minimum level that is used in a particular composition should be effective to provide a conditioning benefit. The maximum level that can be used is not limited by theory, but rather by practicality. It is generally unnecessary and expensive to use levels in excess of about 10% and, depending on the type of agent (polymeric conditioners being most prone), such high levels can cause an undesirable weighting down of the hair.

Conditioning agents suitable for use herein are selected from silicone materials, fatty alcohols, polymeric resins, polyol carboxylic acid esters, cationic polymers, insoluble oils and oil derived materials and mixtures thereof.

Preferred conditioning agents are selected from silicone materials, especially non-volatile silicone and amino functionalised silicones, cationic surfactants, cationic polymers and mixtures thereof.

In another embodiment of the present invention the hair colouring or bleaching compositions of such kits may optionally further comprises a colour refresher composition. Such colour refresher compositions comprise at least one preformed dye and may be applied to the hair immediately after the oxidative colour i.e. from about 1 minute after oxidative hair dye or bleach application to about 60 days after the application. These colour refresher composition can be used to increase the initial colour obtained and or boost the colour during the wash and style cycle until the next oxidative colouring or bleaching event.

In another embodiment of the present invention the composition of the kit may comprise at least one chelant. The chelants are comprised in an amount sufficient to reduce the amount of metals available to interact with formulation components, particularly oxidizing agents, more particularly peroxides. The amount will range from at least about 0.25%, preferably at least about 0.5%, by weight, of the composition. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

The hair colouring or bleaching compositions of such kits may comprise at least one radical scavenger. As used herein the term radical scavenger refers to a species that can react with a radical to convert to a less reactive species by a series of fast reactions. The radical scavenger is comprised from about 0.1% to about 10%, preferably from about 1% to about 7%, by weight of the composition. Preferred radical scavengers may be selected from the classes of alkanolamines, amino sugars, amino acids and mixtures thereof, and may include, but are not limited to: monoethanolamine, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol and mixtures thereof.

In another embodiment of the present invention the hair colouring or bleaching compositions of such kits may optionally further comprises a tool to apply the pre-treatment composition to the hair. The tool may also be suited to contain and dispense the pre-treatment composition on the hair during use.

These tools or devices can come in the form of separate articles which may be used independently or in combination with one another. The most common tool or device which can be used for the present invention involves storing the pre-treatment composition in a container such as a bottle, tube, aerosol, or a sachet.

Another system utilises one or more manually actuated pumps. The product may be contained in a collapsible sachet. When the consumer actuates the pump, the liquid inside the pump is dispensed. As the manually actuated pump returns to the upright position it forces product from a collapsible sachet. A dual system may be installed whereby two sachets and two pumps are used to mix and deliver two pre-treatment compositions to the hair. A single pump connected to two or more sachets may deliver the product by incorporating the mixing point within the pump.

These complex systems offer the advantage of product application independently of the orientation of the product.

The tools and devices described herein above can also be used in combination with a tool or devices to aid application of the pre-treatment composition onto the hair. These tools or devices may be of a very simple nature such as a nozzle attached to one of the containers described above or a separate applicator device such as a comb or brush. Such combs and brushes can be adapted in order to achieve particular effects. For example the tools may be suitable to perform quick and even coverage or root/hairline touch up, or highlights or streaks.

In another embodiment, the container described above may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip and or streaks. The comb may be provided on the container such as to facilitate easy application and may be positioned vertically (so called verticomb) or at an angle to allow the consumer to access all areas. All tools and devices may be designed to have inter-changeability, so that a range of different tools and devices for different hair application can be provided to the consumer to achieve different results.

The organic solvents may be comprised as individually packaged components in separate containers of the kits described above.

Each kit may comprise one or more single packaged compositions of organic solvents and each single packaged composition may comprise either one or a blend of different organic solvents having similar log P properties.

The organic solvent pre-treatment compositions packaged in separate containers may be formulated as solutions of one or more additional components.

The additional component formulated with the pre-treatment composition may include, but are not limited to, buffering agents, colouring agents thickeners, solvents, enzymes, anionic, non ionic, amphoteric and cationic surfactants, carriers, antioxidants, stabilizers, perfumes, masking fragrances, herb and plant extracts, pearlescent, opacifiers, hair swelling agents and/or polymers, humectants, moisturizers, viscosity enhancers, gelling agents, chelators, UV filters, antimicrobials, preservatives, proteins or mixtures thereof.

Thickening agents may be used to increase the viscosity of the organic solvent used in the pre-treatment composition to improve the retention onto the hair during application.

The thickening agents may be comprised in concentrations of at least about 0.1% of the total pre-treatment composition. Thickeners are preferably comprised in an amount sufficient to provide the composition with a viscosity of from about 1 Pa·s to about 10 Pa·s (about 1000 to about 10,000 cP) at 26° C. in order to provide a composition that can be readily applied to the hair without dripping.

A non-exclusive list of thickeners for use herein include xanthan, guar, hydroxypropyl guar, scheroglucan, methyl cellulose, ethyl cellulose (commercially available as Aquacote®), hydroxyethyl cellulose (Natrosol®), carboxymethyl cellulose, hydroxypropylmethyl cellulose, microcrystalline cellulose, hydroxybutylmethyl cellulose, hydroxypropyl cellulose (Klucel®), hydroxyethyl ethyl cellulose, cetyl hydroxyethyl cellulose (Natrosol® Plus 330), N-vinylpyrollidone (Povidone®), Acrylates/Ceteth-20 Itaconate Copolymer (Structure® 3001), Hydroxypropyl starch phosphate (Structure® ZEA), polyethoxylated urethanes or poly carbamyl polyglycol ester (e.g. PEG-150/Decyl/SMDI copolymer=Aculyn® 44, PEG-150/Stearyl/SMDI copolymer=Aculyn 46®), trihydroxystearin (Thixcin®) acylates copoylmer (e.g Aculyn® 33) or hydrophobically modified acrylate copolymers (e.g. Acylates/Steareth-20 Methacylate Copolymer=Aculyn® 22).

Experimental

All results discussed herein were obtained by testing the solvents according to the following protocols. The solvent tested can be obtained from any usual supplier.

Hair Treatment Protocol

For each solvent tested, virgin natural white hair was used. 'Virgin hair' means hair that has never been treated chemically and can be bought, for example, at Hugo Royer International Ltd, 10 Lakeside Business Park, Swan Park, Sandhurst, Berkshire, GU47 9ND. This particular substrate was chosen as it is non-pigmented and thus the maximum impact of the solvents on the subsequent dyeing process can be observed. The switches weighed about 1.5 grams each and are treated according to the following, protocol. Switches were pre-treated by soaking the switch for 5 minutes in a small beaker containing approximately 20 ml of solvent. The hair switch was removed after this time and any excess solvent was wiped from the hair by dragging it between two gloved fingers. The hair switch was then coloured using a commercially available level 3 oxidative hair colorant (Nice n' Easy in this case) for 30 minutes at 30° C. After this time the hair switch was removed from the temperature controlled unit and the hair colorant washed off. The hair switch was shampooed to removed any remaining hair colourant product and then left to dry in front of cold air fans. Upon drying the colour of the hair was measured using a Minolta 1600d Spectrophotometer and the subsequent K/S value calculated.

Measurement of the solvent's impact on the subsequent dye performance. In order to understand the performance of a solvent, be it 'dye up' or 'dye down' the measure K/S has been used. This gives an accurate measure of the intensity of the colour delivered and is described in further detail below;

K/S Measurement of Shade Depth–K/S is derived from the Kubelka-Munk equation (Kubelka and Munk, Zeit. Für.Tekn-.Physik, 12, p. 593 (1931)) and describes apparent colour strength. K/S at each wavelength is calculated as:

$$K/S = (1-R)^2 / 2R$$

where R is reflectance of the incident light from the treated hair sample for each given wavelength.

To reduce the spectral data to a single value, an average-sum-weighted K/S value is used. The spectral K/S values are multiplied by the human matching fractions; each result is integrated, added together, and then divided by the spectral sampling rate.

The differing solvents can be used to either increase the amount of dye delivered to the hair fibre vs. no pre-treatment referred to herein as 'dye-up' or they can decrease the amount of dye delivered to the hair fibre vs. no pre-treatment, herein referred to as 'dye down'. Table 1 shows examples of solvents that have positive log P values (hydrophobic) and increase dye uptake into the hair, whilst Table 2 shown organic solvent that have a negative log P (hydrophilic and that are capable of decreasing dye uptake into the hair

TABLE 1 solvents capable of increasing dye uptake

| Solvent | K/S vs. DI Water | Log P |
|---|---|---|
| Cyclohexanone[1] | +17% | +0.76 |
| n-Butanol[2] | +33% | +0.88 |
| 4-methyl-2-pentanone[3] | +66% | +1.25 |

[1]ReagantPlus ™ 99.8%;
[2]ACS Reagent ≧ 99.4%;
[3]CHROMASOLV ® for HPLC, ≧ 99.5%;

all available from Sigma-Aldrich Co. Ltd, The Old Brickyard, New Road, Gillingham, SP8 4XT, United Kingdom.

TABLE 2 solvents capable of decreasing dye uptake

| Solvent | K/S vs. DI Water | Log P |
|---|---|---|
| Glycerine[4] | −40% | −2.32 |
| Diethyleneglycol[5] | −50% | −1.51 |
| Dipropyleneglycol[6] | −43% | −0.66 |

[4]Glycerine ReagentPlus ™, ≧ 99%;
[5]Diethylene glycol, ReagentPlus ™, 99%;
[6]Dipropyleneglycol 99%;

all available from Sigma-Aldrich Co. Ltd, The Old Brickyard, New Road, Gillingham, SP8 4XT, United Kingdom.

In order to show that increasing amounts of an organic solvent in the pre-treatment composition have an effect on the dye uptake, increasing amounts of glycerine (% wt.) were mixed with de-ionised water. The resulting pre-treatment compositions were tested on the dye uptake performance and the results are shown in Table 3 below. Table 3 clearly shows that as the glycerine content increases in the pre-treatment compositions, the lower is the dye penetration into the hair.

TABLE 3

Impact of glycerine weight on the dye uptake

| Glycerine Content (% wt.) | K/S vs. DI Water |
|---|---|
| 10 | −2% |
| 25 | −4% |
| 50 | −20% |
| 70 | −43% |

Table 4a and 4b shows examples of pre-treatment compositions that can be utilized before any dyeing event on any type of hair.

TABLE 4a

| | Formulation Number | | | | | | | | | | | | | |
|---|---|---|---|---|---|---|---|---|---|---|---|---|---|---|
| Ingredients | 1 | 2 | 3 | 4 | 5 | 6 | 7 | 8 | 9 | 10 | 11 | 12 | 13 | 14 |
| Carboxymethyl cellulose[1] | 0.5 | — | — | — | — | — | — | — | — | — | 0.5 | 1.0 | — | — |

TABLE 4a-continued

| Ingredients | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Xanthan Gum[2] | — | — | — | — | 0.5 | 1.0 | — | — | — | — | — | — | 0.5 | — |
| Acrylates C10-30 Alkyl acrylate Crosspolymer[3] | — | — | 0.5 | 0.5 | — | — | 0.5 | 0.5 | 0.5 | 0.5 | — | — | — | — |
| Triethanolamine | — | — | 0.1 | 0.1 | — | — | 0.1 | 0.1 | 0.1 | 0.1 | — | — | — | — |
| Cyclohexanone | — | — | — | — | 10 | 25 | — | — | — | — | — | — | — | — |
| n-Butanol | — | — | — | — | — | — | 50 | 70 | — | — | — | — | — | 25 |
| 4-Methyl-2-Pentanone | — | — | — | — | — | — | — | — | 50 | 70 | — | — | — | 25 |
| Glycerine | 10 | 25 | 50 | 70 | — | — | — | — | — | — | — | — | 25 | — |
| Diethyleneglycol | — | — | — | — | — | — | — | — | — | — | 50 | 70 | 25 | — |
| Preservatives | 0.7 | 0.7 | 0.7 | 0.7 | 0.4 | 0.7 | 0.7 | 0.7 | 0.7 | 0.7 | 0.7 | 0.5 | 0.4 | 0.2 |
| Fragrance | 0.1 | 0.2 | 0.1 | 0.2 | 0.1 | 0.3 | 0.4 | 0.1 | 0.2 | 0.1 | 0.3 | 0.4 | 0.2 | 0.1 |
| Water | qs | qs | qs | qs | qs | qs | qs | qs | qs | qs | qs | qs | qs | qs |

TABLE 4b

|  | 15 | 16 | 17 | 18 | 19 | 20 | 21 | 22 |
|---|---|---|---|---|---|---|---|---|
| Carboxymethyl cellulose[1] | 0.5 | — | — | — | — | — | — | — |
| Xanthan Gum[2] | — | — | — | — | 0.5 | 1.0 | — | — |
| Acrylates C10-30 Alkyl acrylate Crosspolymer[3] | — | — | 0.5 | 0.5 | — | — | 0.5 | — |
| Triethanolamine | — | — | 0.1 | 0.1 | — | — | 0.1 | — |
| Cyclohexanone | — | — | — | — | 10 | 25 | — | — |
| n-Butanol | — | — | — | — | — | — | 98.99 | 100 |
| 4-Methyl-2-Pentanone | — | — | — | — | — | — | — | — |
| Glycerine | 98.99 | 100 | — | — | — | — | — | — |
| Diethyleneglycol | — | — | — | — | — | — | — | — |
| Preservatives | 0.3 | — | 0.7 | 0.7 | 0.7 | 0.7 | 0.2 | — |
| Fragrance | 0.1 | — | 0.2 | 0.3 | 0.2 | 0.3 | 0.1 | — |
| Water | qs | — | qs | qs | qs | qs | qs | — |

[1]Carboxymethyl cellulose available as Natrosol Hydroxyethylcellulose,
[2]Xanthan Gum available as Ketrol CG T,
[3]Acrylates/C10-30 Alkyl Acrylate Crosspolymer available as Carbopol ETD 2020 Polymer.

The dimensions and values disclosed herein are not to be understood as being strictly limited to the exact numerical values recited. Instead, unless otherwise specified, each such dimension is intended to mean both the value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for treating hair consisting of water and the steps of
   a) contacting the hair with a pre-treatment composition comprising at least one organic solvent selected from the group consisting of glycerine, diethyleneglycol, dipropylene glycol and mixtures thereof, wherein said organic solvent is present in said pre-treatment composition at a level of from about 50% to about 100% by weight of the pre-treatment composition, and then
   b) applying a hair dyeing composition to the hair.

2. The method according to claim 1, wherein said pre-treatment composition applied in step a) is either left in place on the hair or is rinsed off the hair before step b).

3. The method according to claim 1, wherein the pre-treatment composition is left on the hair for from about 1 to about 60 minutes.

* * * * *